United States Patent

Stoy et al.

Patent Number: 5,368,048
Date of Patent: *Nov. 29, 1994

[54] METHOD OF MAKING RADIO-OPAQUE TIPPED, SLEEVED GUIDEWIRE AND PRODUCT

[76] Inventors: George P. Stoy, 78 Princeton Ave., Rocky Hill, N.J. 08553; Kenneth H. Blashka, 35 Princeton Rd., Elizabeth, N.J. 07208

[*] Notice: The portion of the term of this patent subsequent to Jun. 8, 2010 has been disclaimed.

[21] Appl. No.: 48,240
[22] Filed: Apr. 19, 1993
[51] Int. Cl.⁵ .................. A61M 25/00; B32B 31/00
[52] U.S. Cl. .................. 128/772; 128/657; 156/86
[58] Field of Search ............. 604/95, 164, 265, 280, 604/282; 128/656–658, 772; 600/7, 8; 156/84–86; 264/342 R

[56] References Cited

U.S. PATENT DOCUMENTS

| | | |
|---|---|---|
| 3,566,874 | 3/1971 | Shepherd et al. |
| 3,695,921 | 10/1972 | Shepherd et al. |
| 3,861,396 | 1/1975 | Vaillancourt et al. |
| 3,862,452 | 1/1975 | Wichterle et al. |
| 3,975,350 | 8/1976 | Hudgin et al. |
| 4,026,296 | 5/1977 | Stoy et al. |
| 4,100,309 | 7/1978 | Micklus et al. |
| 4,119,094 | 10/1978 | Micklus et al. |
| 4,430,083 | 2/1984 | Ganz et al. ............. 128/772 |
| 4,456,017 | 6/1984 | Miles ..................... 604/95 |
| 4,527,293 | 7/1985 | Eckstein et al. |
| 4,545,390 | 10/1985 | Leary. |
| 4,579,127 | 4/1986 | Haacke. |
| 4,581,390 | 4/1986 | Flynn ..................... 604/280 |
| 4,721,117 | 1/1988 | Mar et al. ............... 604/282 |
| 4,798,593 | 1/1989 | Iwatschenko. |
| 4,811,743 | 3/1989 | Stevens. |
| 4,815,478 | 3/1989 | Buchbinder et al. |
| 4,826,485 | 5/1989 | Johnson. |
| 4,834,709 | 5/1989 | Banning et al. |
| 4,867,173 | 9/1989 | Leoni. |
| 4,884,579 | 12/1989 | Engelson. |
| 4,895,168 | 1/1990 | Machek. |
| 4,925,445 | 5/1990 | Sakamoto et al. |
| 4,940,633 | 7/1990 | Hermansen et al. ..... 428/324 |
| 4,991,602 | 2/1991 | Amplatz et al. ......... 128/657 |
| 5,015,238 | 5/1991 | Solomon et al. |
| 5,171,383 | 12/1992 | Sagaye et al. .......... 128/772 |
| 5,217,026 | 6/1993 | Stoy et al. .............. 128/657 |
| 5,256,158 | 10/1993 | Tolkoff et al. .......... 604/280 |
| 5,267,574 | 12/1993 | Viera et al. ............. 604/280 |

Primary Examiner—C. Fred Rosenbaum
Assistant Examiner—Mark Bockelman
Attorney, Agent, or Firm—Kenneth P. Glynn

[57] ABSTRACT

The present invention is a method of making a radio-opaque tipped, sleeved guidewire. It includes providing a bendable core piece of a predetermined length, having a control end and a distal end and having a predetermined core diameter, and providing a shrinkable polymeric sleeve formed of a first polymer composition having a first diameter at least as large as said core diameter and having a second, smaller diameter from shrinking said second diameter, which is less than said core diameter. The polymeric sleeve is placed over the core piece while the polymeric sleeve has its first diameter, so as to have one end of the polymeric sleeve cover at least a portion of the distal end of the core piece. Next, a mixture of a radio-opaque metal powder and a second polymer composition is provided. The second polymer composition is capable of forming a physical bond with the first polymeric composition of the polymeric sleeve. The mixture is inserted into the overhanging polymeric sleeve at the distal end of the core piece and the polymeric sleeve is shrunk to its second, smaller diameter. The physical bond is formed between the first polymer composition and the second polymer composition. The present invention is also directed to the resulting guidewire products.

29 Claims, 1 Drawing Sheet

METHOD OF MAKING RADIO-OPAQUE TIPPED, SLEEVED GUIDEWIRE AND PRODUCT

BACKGROUND OF THE INVENTION

1. Field of the Invention

The present invention relates to guidewires and methods of making guidewires. In particularly, the present invention relates to methods of making radio-opaque tipped guidewires with polymer coatings and the resulting products.

2. Information Disclosure Statement

Guidewires are devices designed to facilitate insertion and placement of various tubular instruments such as catheters, stents, drains, cystoscopes, dilators and other items designed for penetration into various organs or body cavities to perform delivery or withdrawal of fluids, securing patency or access, removal of tissues for diagnostics or surgery, facilitating entry of other devices, etc.

In some procedures, guidewires are typically placed within the body at the desired location in advance, creating a convenient pathway for tubular instruments which are slid into their proper place over it. In other procedures, guidewires are inserted into the desired location together with the tubular instrument or device, e.g. a catheter, providing temporary stiffening needed for the insertion. Once the tubular instrument is in place, the guidewire may be removed and the instrument used for its primary purpose.

Guidewires are of various configurations, made from various materials and are made for various purposes. Their various kinds are sometimes also called Seldinger wires, introducers, mandrels, stylets, etc. In the present specification, all such insertion devices for carrying tubular instruments to a desired body location are generally referred to as "guidewires".

In spite of their diverse shapes, sizes and uses, all guidewire devices have several problems in common.

Each of these devices is required to penetrate through tight passages, which are often long and tortuous. This penetration is hindered by friction. The friction complicates the device placement, and may even cause injury to certain surfaces (e.g. tracheal, urethral or vascular wall). Therefore, the outer surfaces have to have low friction against contacting surfaces (e.g. vascular walls, inner walls of catheters or other instruments).

The low friction can be to some extent achieved by creating smooth, high quality surfaces (e.g. polished stainless steel, smooth plastic coatings, etc.). Since this is not always possible or sufficient, guidewires are often equipped with surface layers of various low-friction materials.

Another problem with guidewires relates to the need to track guidewire location to assure that the guidewire is following the desired path within the body. This is accomplished, for example, by the use of a radio-opaque wire core or a radio-opaque tip.

The following represents the state of the prior art with respect to plastic or polymer coated guidewires:

U.S. Pat. No. 4,579,127 of Claus Haacke directed to a "Mandrel For Hose Type Catheters And Body Probes", describes guidewires made from wound metal wires equipped with thin plastic coatings which follow the contours of the wire surfaces.

As another example, U.S. Pat. No. 4,811,743 of Robert C. Stevens describes a "Catheter Guidewire" consisting of a metal flexible core with spherical tip surrounded by sheath of tightly wound wire. The outside sheath surface is provided with a thin (<0.001") Teflon ® coating.

Also, U.S. Pat. No. 4,826,485 of Theodore D. Johnson relates to a "Device For Guiding Tubings" and describes a stylet for introducing, for example, gastric feeding tubes. The cable is made from metal or plastic wire, which forms the central portion of the stylet, which may be coated with an inert polymeric material such as medical grade Teflon ®. The thickness of the coating is typically 0,002-0.004". Likewise, U.S. Pat. No. 4,834,709 of Robert D. Banning, et al. describes a performable silicone catheter with a malleable stylet, comprising a malleable wire core and a plastic covering made of a polypropylene (preferred), polyethylene, Teflon ®, etc. The covering can be formed either as a coating, or from a pre-extruded plastic tubing which has larger lumen than the outer diameter of the wire so that it can be readily inserted.

Also, U.S. Pat. No. 4,867,173 of Gianni Leoni is directed to a "Steerable Guidewire" and describes a small-diameter guidewire for percutaneous translumenal coronary angioplasty (PTCA). The main core wire is said to be coated with a frictionless material such as Teflon ®. Another U.S. Pat. No. 4,545,390, of James J. Leary describes a guidewire with a Teflon ®-coated main core wire.

Sometimes the plastic cover or coating has primary purpose of providing additional safety. For instance, U.S. Pat. No. 4,925,445 of Hidetoshi Sakamoto et al. entitled "Guide Wire For Catheters" describes a guidewire made from "super-elastic" memory titanium nickel or other metal alloys. It is provided with a plastic coating to increase its resistance against buckling. The coating can be made from an elastomeric or a composite material of a synthetic resin material including polyethylene, polyvinyl chloride, TEFLON ®, silicone rubber, etc.

U.S. Pat. No. 4,895,168 of James E. Machek entitled "Guidewire With Movable Core And External Tubular Safety Cover" describes a guidewire with a wound wire casing covered by a plastic safety cover which is supposed to retain fragments of broken wire. This safety cover is preferably from heat-shrinkable TEFLON ® tubing.

U.S. Pat. No. 4,884,579 of Erik T. Engelson entitled "Catheter Guide Wire" describes a guidewire with three sections of progressively decreasing rigidity. The central section has surface which is more lubricous than surfaces of adjacent proximal and distal sections. The intermediate section comprises a wirecore segment with flexible polymer covering which encases the intermediate core segment. The covering polymeric material provides appropriate flexibility to this section. The flexible polymer covering can be applied by spraying or dipping, or by a pre-formed tube which can be attached by heat shrinking over the core wire. This section has also low friction polymer surface. This can be achieved by using a covering made from a polymer which has a low friction in itself, such as TEFLON ®. Alternatively, this polymer covering can be provided with a surface coating of a highly hydrophilic, low friction polymer, such as polyvinylpyrrolidine, polyethyleneoxide or poly(2-HEMA). Such a surface coating can be applied by spraying or dipping according to known methods. There is a radio-opaque metal coil at the distal end which is also polymer coated.

This last example suggests the use of hydrophilic polymer surface coatings which have various advantages. For instance, hydrophilic coatings typically have lower wet friction than, e.g. Teflon ®. They have lesser adhesion to tissue, to thrombus or to clot so that they are less prone to clogging, sticking to the wound, etc. Still another advantage is that the hydrophilic polymer layers can be used as a carrier for various water-soluble drugs, such as antibiotics.

Because of these advantages, hydrogel-coated surgical tubular devices are often suggested in the prior art. (For instance: U.S. Pat. No. 3,566,874 of Francis E. Gould and Thomas H. Shepard entitled "Catheter", U.S. Pat. No. 3,862,452 Otto Wichterle, et als. entitled "Hydrogel Substitutes For Tubular Somatic Organs", U.S. Pat. No. 3,861,396 by Vincent L. Vaillancourt, et als. entitled "Drainage Tube", U.S. Pat. No. 4,026,296 of Artur Stoy, et als. entitled "Hydrophilic Surgical Tubular Device", U.S. Pat. No. 4,527,293 Eugene C. Eckstein, et als. entitled "Hydrogel Surface Of Urological Prothesis", U.S. Pat. No. 5,015,238 of Donald D. Solomon et als. entitled "Expandable Obturator And Catheter Assembly Including Same", to name only some.)

To this purpose, various hydrogel coating systems have been developed, based on polymerizable acrylic coatings (e.g. U.S. Pat. No. 3,695,921 of Francis E. Gould and Thomas H. Shepard entitled "Method Of Coating A Catheter"), on hydrophilic polyurethanes (e.g. U.S. Pat. No. 3,975,350 of Donald E. Hudgin and Edgar A. Blair entitled "Hydrophilic Or Hydrogel Carrier Systems Such As Coatings, Body Implants And Other Articles"), crosslinked poly(vinylpyrrolidine) (e.g. in U.S. Pat. No. 4,100,309 of Michael J. Miclus, et al entitled "Coated Substrate Having A Low Coefficient Of Friction Hydrophilic Coating And A Method Of Making The Same"; and U.S. Pat. No. 4,119,094 of Michael J. Mickius, et al entitled "Coated Substrate Having A Low Coefficient Of Friction Hydrophilic Coating And A Method Of Making The Same", etc.).

Such hydrophilic coatings can be applied also to guidewires. For instance, U.S. Pat. No. 4,798,593 of Peter Iwatschenko entitled "Stiffening Of Probes" describes mandrels for catheters etc. consisting of a wire element with coating of a biocompatible material of which at least the surface in hydrophilic. The coating may be applied by dipping or spraying. A specific hydrophilic polymer mentioned is gelatin softened, e.g., by glycerol.

In another example, U.S. Pat. No. 4,815,478 Maurice Buchbinder, et al entitled "Steerable Guidewire With Deflectable Tip" describes a steerable guidewire consisting of a tubing (preferably flexible metal tubing) which provides for steering of a deflection wire, and a spring coil distal end. It is mentioned that it is advantageous to cover whole length of the guidewire, preferably including the tip, with a lubricious coating made from polymer such as Teflon ® or a hydrogel and to use a radio-opaque material such as a platinum alloy for the spring coil at the distal end.

In addition to the above, the following Unites States Patents describe guidewires with radio-opaque tips which include wire coils or springs formed of radio-opaque metals;
1) U.S. Pat. No. 4,538,622
2) U.S. Pat. No. 4,748,986
3) U.S. Pat. No. 4,846,186
4) U.S. Pat. No. 4,922,924
5) U.S. Pat. No. 4,998,916
6) U.S. Pat. No. 5,135,503

Not withstanding the significant prior art relating to coated guidewires and to radio-opaque tips, the prior art neither teaches nor suggests the present invention method of making radio-opaque tipped, sleeved guidewires and the resulting products.

SUMMARY OF THE INVENTION

The present invention is a method of making a radio-opaque tipped, sleeved guidewire. It includes providing a bendable core piece of a predetermined length, having a control end and a distal end and having a predetermined core diameter, and providing a shrinkable polymeric sleeve formed of a first polymer composition having a first diameter at least as large as said core diameter and having a second, smaller diameter from shrinking said second diameter, which is less than said core diameter.

The polymeric sleeve is placed over the core piece while the polymeric sleeve has its first diameter, so as to have one end of the polymeric sleeve extend to cover at least a portion of the distal end, but preferably extend beyond and overhang the distal end of the core piece. Next, a mixture of a radio-opaque metal powder and a second polymer composition is provided. The second polymer composition is capable of forming a physical bond with the first polymeric composition of the polymeric sleeve. The mixture is inserted into the overhanging polymeric sleeve at the distal end of the core piece and the polymeric sleeve is shrunk to its second, smaller diameter. The physical bond is formed between the first polymer composition and the second polymer composition. The present invention is also directed to the resulting guidewire products.

BRIEF DESCRIPTION OF THE DRAWINGS

The present invention will be more fully appreciated when the specification herein is taken in conjunction with the drawing appended hereto, wherein.

DETAILED DESCRIPTION OF THE PRESENT INVENTION

Figure 1:
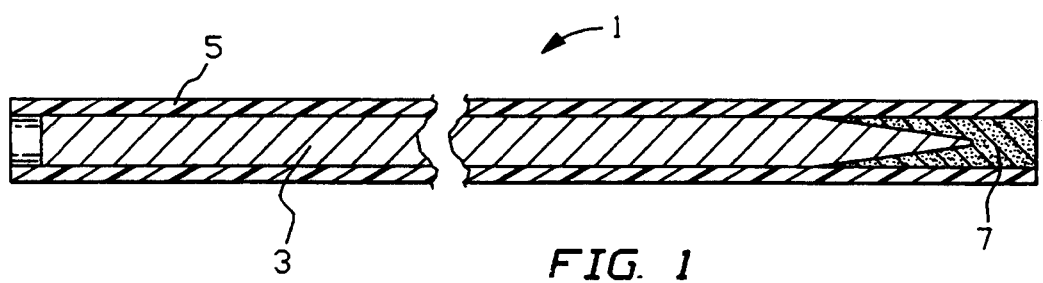
FIG. 1 shows a side cut view of a preferred embodiment guidewire of the present invention with a tapered distal end.

The present invention is a method of making a radio-opaque tipped, sleeved guidewire and the guidewire itself.

The method of the present invention involves, initially, the selection of a core piece, a first polymer composition for a sleeve, a second polymer composition for intermixing with a radio-opaque powdered metal for insertion into a distal end of the sleeve, and the powdered metal itself.

The core piece may be any known or to be developed core piece, as long as it has the required rigidity, flexibility, bendability and torque limits necessary for the desired application. Such core pieces are well known and may be rigid plastic or metal, and is usually a metal wire. Such metal core pieces may be formed of stainless steel, nickel alloys, titanium alloys, copper alloys, spring steel, and the like. The core pieces may have a diameter of about 0.006 inches up to about 0.5 inches or more. For example, stylet types would be larger and catheter guidewires would be in the lower diameter range, e.g. 0.006 to 0.03 inches. Such core pieces may be as long as desired to accomplish its purpose, and may be short, e.g. two or three feet, or long, e.g. up to five or six feet, or more, depending upon the particular use.

The first polymer composition is used to form a sleeve for the core piece and, thus, desirably has some shrinkability, strength, flexibility, adhereability to the core piece, and lubricity. These would include urethane polymers, silicone polymers, polyacrylonitrile polymers, and any other polymer that can be swollen with known solvents, copolymers of these, cross-linked polymers, etc. Preferred are the polymers which contain polyacrylonitriles, especially copolymers.

Examples of such polyacrylonitriles are block copolymers of polyacrylonitriles and derivatives of polyacrylic acid, e.g. amides, esters, amidines, and others known in the art.

Preferred are hydrogels, which impart lubricious characteristics, and which form strong physical bonds yet are compatible with internal body applications due to their softness and other gel-like characteristics. Thus, hydrogel polyacrylonitrile-containing polymers and copolymers are preferred.

The first polymer composition and the second polymer composition must be capable of forming a physical bond. By "physical bond" is meant any connection between the two polymer compositions which will hold them together during the usage of the guidewire. Rigorous standards of usage are known to be applicable to guidewires to assure that they do not tear, break of otherwise come apart during usage and do not leave any residue within the body.

The physical bonding created between the first polymer composition and the second polymer composition may be formed by methods such as chemical bonding, e.g. crosslinking, adhesion, fusion, network polymer interlinking or interweaving and the like.

The second polymer composition used in the present invention method must be a polymer which is capable of physical bonding of the first polymer composition sleeve. These include those of the first polymer composition group but should preferably be in a more active form, e.g. more dissolved in a solvent solution, less completely polymerized, having more pendant chains, having ionic chains, being capable of network polymerizing, etc.

The second polymer composition may preferably be block copolymers of polyacrylonitriles and derivatives of polyacrilic acid, e.g. amides, esters, amidines, and others known in the art. Preferably, it is one containing polyacrylonitrile, its copolymers and its hydrophilic, hydrophobic and hydrophilic/hydrophobic polymers. Hydrogels are preferred.

The radio-opaque metal powder is any one or more metals which will appear on x-ray and other tracking systems and generally includes any of the heavy metals. Preferred are non-toxic heavy metals, especially tungsten, platinum, tantalum and gold, as well as workable metal compounds which are radio-opaque or would yield radio-opaque results. Particle size may vary from less than a micron to tens of microns or greater, but is preferably in the range of about 0.1 to about 50 microns, especially about 0.5 to about 20 microns.

In the method of the present invention, a sleeve is formed with the first polymer composition for fitting over the core piece. This may be formed with the first polymer composition for fitting over at least a portion of the core piece. This may be formed in an enlarged form and shrunk after being placed on the core piece, or it may be formed in its smaller form, subsequently swollen, and then shrunk on the core piece.

The sleeve may be shorter than the core piece to cover only a portion (including the distal end), may be about equal length with the core piece, or may be longer. Preferably, the sleeve is longer than the core piece and is allowed to overhang at the distal end. The sleeve may be excessively long and trimmed at the end of the preparation method, or it may be formed to a predetermined desired length. It is formed to achieve a predetermined inner diameter equal to or greater than the diameter of the core piece and is shrinkage to a tight fit, e.g. it would shrink to a diameter smaller than the core piece if not shrunk on the core piece.

The radio-opaque mixture is formed of the second polymer composition and one or more radio-opaque metal powders. The polymer is usually in a fluid form, e.g. solution or emulsion, and then mixed with the metal. The metal is, by weight, from as low as 20 percent based on the weight of the polymer and metal or as high as 90 percent or more. Higher percentages, e.g. 50 percent to 85 percent by weight is preferred to provide enough radio-opaque material in the distal end of the guidewire to permit even weak visualization systems to be used.

After the radio-opaque mixture is formed, it is placed into the distal end sleeve, e.g. the overhang. The sleeve is shrunk and the physical bond is formed, e.g. chemically, by polymer interweave, fusing or other.

The guidewire sleeve may be shrunk, in preferred embodiments, by solvent extraction. This may be solvent to water or solvent to a second solvent, as long as shrinking results. The stoichiometry and properties of particular polymer compositions will dictate the solvent levels and solvent choices as well as the extraction medium. In such embodiments the solvent extraction, preferably, also initiates the physical bond formation of the first polymer composition and the second polymer composition.

The following solvents are effective for polyacrylonitrile at either room temperature or elevated temperatures; dimethylformamide, dimethylpolyacrylonitrile, dimethylthioformamide, dimethylacetamide, N-methyl-$\beta$-cyanoethyl formamide, $\alpha$-cyanoacetamide, tetramethyl oxamide, malononitrile, fumaronitrile, succinonitrile, adiponitrile, $\alpha$-chloro-$\beta$-hydroxypropionitrile, $\beta$-hydroxypropionitrile, hydroxyacetonitrile, N,N-di(cyanomethyl)aminoacetonitrile, $\epsilon$-caprolactam, bis($\beta$-cyanoethyl)ether, y-butyrolactone, propiolactone, 1,2,3,-tetracyanopentane, tetramethylene sulfoxide, dimethyl sulfoxide, 2-hydroxyethyl methyl sulfone, methyl ethyl sulfolane, m-nitrophenol, p-nitrophenol, (o-,m-,p-)phenylene diamine, methylene dithiocyanate, trimethylene dithiocyanate, dimethyl cyanamide, ethlene carbonate, proplyene carbonate, succinic anhydride, maleic anhydride, certain N-nitro- and nitrosoalkyl amines, some formulated primary and secondary amines, pyrrolidinone derivatives, concentrated sulfuric acid or nitric acid, and concentrated aqueous solutions of LiBr, NaCNS, or $ZnCl_2$. Copolymers of acrylonitrile are often soluble in dioxane, chlorobenzene, cyclohexanone, methyl ethyl ketone, acetone, dimethylformamide, butyrolactone, and tetrahydrofuran.

After solvent extraction, the guidewire may be dried, e.g. at 100° C. down to as low as room temperature. Drying Time varies depending upon the polymers, the size of the sleeve and the temperature selected.

Plasticizer may be applied to the sleeve after solvent extraction, before or after or without heated drying. Such plasticizers include glycerol, monoacetin, diacetin, polyethylene glycol and mixtures thereof.

The resulting product is a lubricious, flexible, torqueable sleeved guidewire with a radio-opaque tip.

The following Examples are presented for illustration purposes only, and the invention should not be construed to be limited to these particular examples:

EXAMPLE I

A radio-opaque tipped, sleeved guidewire 1 of the present invention shown in FIG. 1 is made as follows:

A stainless steel core piece of 150 cm in length has a diameter of 0.020 inches. This is its maximum and fixed diameter from its control end to the last 10 cm at the distal end. This last 10 cm tapers from 0.020 inches down to 0.002 inches.

A polyacrylonitrile-acrylamide copolymer hydrogel sold as PANAMEX TM by Kingston Technologies, Inc. of Dayton, N.J. is formed initially into a sleeve with a small inner diameter of 0.017 inches and an outer diameter of 0.037 inches. It is enlarged to an inner diameter of about 0.024 inches and an outer diameter of 0.043 inches so as to fit over the gore piece. The sleeve has a length of about 175 cm. enlargement is done by soaking in an aqueous NaSCN solution (38 percent by weight).

The sleeve is placed over the core piece with overhang at both ends, but this is only essential at the distal end.

A 55 percent by weight solution of NaSCN in water is mixed 90 percent by weight with 10 percent by weight of a polyacrylonitrile hydrogel polymer having pendant anionic and cationic chains, known as HYPAN 86 TM by Kingston Technologies, Inc. above. This solution is mixed with 60 percent by weight of tungsten powder, it is loaded into the distal end overhanging sleeve with a syringe, including around the entire tapered portion of the core piece.

The guidewire 1 with its core piece 3 its first polymer composition sleeve 5 and its second polymer composition-containing mixture 7 with radio-opaque tungsten metal powder is next placed in water to extract the NaSCN solvent. This shrinks the sleeve 5 to tightly and fixedly force fit onto core piece 3, having now an outer diameter of about 0.035 inches. Before shrinking the higher concentration of solvent in the second polymer composition has increased the solvent level in the first polymer composition to cause partial dissolving of the first polymer composition. Thus, during extraction the two polymer compositions fuse to one another, creating a tight physical bond.

The resulting guidewire is soaked with a plasticizer, e.g. 70% glycerol in water and thereafter is removed by heating at 60° to 80° C. for about 2 hours.

The final guidewire product has desirable flexibility, bendability, a lubricous surface quality and good torque transmission with a safe, soft radio-opaque distal tip.

EXAMPLE 2

The guidewire described in Example 1 is prepared in the same manner and with the same core piece and sleeve, except that the second polymer composition is a cross-linkable polyacrylonitrile copolymer which is partially polymerized before insertion in the distal end sleeve portion and polymerization is completed thereafter so as to create a network polymer interlinked with the sleeve. The interlinking of network polymers is found to create an effective physical bond for purposes of the present invention guidewire device.

EXAMPLES 3, 4, and 5

The Example 1 guidewire formation is repeated except that dimethyl formamide, zinc chloride, dimethyl sulfoxide, are used in Examples 3, 4, and 5 respectively in place of NaSCN.

EXAMPLE 6

A guidewire is formed in accordance with Example 1 above, except that the polymeric sleeve and the second polymer filler are both polyurethane and the solvents used are different. A polyurethane tubing (Pellethane 2363-55DE available from Dow Chemical Corporation) is formed by extrusion with an inner diameter of 0.017 inches and an outer diameter of 0.032 inches. It is swollen in a solvent mixture of 50% tetrahydrofuran and 50% ethanol until an inner diameter of about 0.023 inches is achieved. This swollen sleeve is placed over a stainless steel core piece having a diameter of 0.020 inches, with the last 2 inches of the core piece tapering down to 0.003 inches.

The second polymer, the one used for the radio-opaque mixture, is the same polyurethane material. A mixture of 10% by weight of the polyurethane, 7% powdered tantalum, and the balance tetrahydrofuran is formed and dispensed into the distal end of the sleeve and over the tapered portion of the core piece. The sleeve is shrunk and the radio-opaque polymer mixture is fused by solvent evaporation at 60° C. for three hours. The resulting guidewire was snipped at the distal end to have the sleeve terminate at the core piece distal end terminus.

EXAMPLE 7

The method of Example 1 is repeated, except that a 50/50 mixture of tantalum and platinum is used in place of tungsten.

EXAMPLE 8

The method of Example 1 is repeated, except that the first polymer composition and the second polymer composition are each only 80 percent or so polymerized prior to use and, after the mixture of the second polymer composition and metal powder is inserted into the sleeve on the core piece, polymerization is catalyzed by ammonium persulfate to interlink and bond the first and second polymer compositions to create a physical bond therebetween.

Obviously, numerous modifications and variations of the present invention are possible in light of the above teachings, it is therefore understood that within the scope of the appended claims, the invention may be practiced otherwise than as specifically described herein.

What is claimed is:

1. A method of making a radio-opaque tipped, sleeved guidewire, which comprises:
   (a) providing a bendable solid core piece of a predetermined length, having a control end and a distal end and having a predetermined core diameter, and providing a shrinkable polymeric sleeve formed of a first polymer composition said first polymer composition being a polyacrylonitrile-containing composition and having a first diameter at least as large as said core diameter and capable of having a second, smaller diameter from shrinkage of said sleeve, wherein said second diameter is less than said core diameter;

(b) placing said polymeric sleeve over said core piece while said polymeric sleeve has its first diameter, and placing it so as to leave one end of said polymeric sleeve covering at least a portion of the distal end of said core piece and so as to leave a portion of said polymeric sleeve overhanging said distal end of said core piece;

(c) providing a mixture of a radio-opaque metal powder and a second polymer composition, said second polymer composition being capable of forming a physical bond with said first polymeric composition of said polymeric sleeve;

(d) inserting said mixture into the overhanging polymeric sleeve at the distal end of said core piece to establish a separate area of said mixture of radio-opaque metal powder and said second polymer composition; and, (e) shrinking said polymeric sleeve to its second, smaller diameter and forming said physical bond between said first polymer composition and said second polymer composition while maintaining said separate area of said mixture of radio-opaque metal powder and said second polymer composition.

2. The method of claim 1 wherein said physical bond is created by chemical interaction between said first polymer composition and said second polymer composition.

3. The method of claim 1 wherein said physical bond is created by solvent extraction from the first polymer composition and the second polymer composition to fuse them together.

4. The method of claim 3 wherein said solvent extraction is accomplished by soaking the guidewire in an aqueous medium.

5. The method of claim 1 wherein said shrinking and forming said physical bond are simultaneously accomplished by solvent extraction wherein excess solvent in said second polymer composition causes a portion of said first polymer composition to dissolve prior to extraction and wherein the extraction causes subsequent fusion between said first polymer composition and said second polymer composition.

6. The method of claim 1 wherein said physical bond is created by forming a polymer network by completion of polymerization of said second polymer composition wherein said network is at least partially interwoven with said first polymer composition.

7. The method of claim 1 wherein said core piece has a fixed predetermined maximum core diameter for most of its length and has a tapered distal end.

8. The method of claim 7 wherein said mixture is inserted into the distal end overhang of said polymeric sleeve, including being inserted around the tapered distal end of said core piece.

9. The method of claim 1 wherein said first polymer composition is a polyacrylonitrile-containing copolymer.

10. The method of claim 1 wherein said first polymer composition is a hydrogel.

11. The method of claim 1 wherein said second polymer composition is a polyacrylonitrile-containing composition.

12. The method of claim 11 wherein said second polymer composition is a polyacrylonitrile-containing copolymer.

13. The method of claim 1 wherein said second polymer composition is a hydrogel.

14. The method of claim 1 wherein said first polymer composition and said second polymer composition are both polyacrylonitrile-containing copolymers.

15. A radio-opaque tipped, sleeved guidewire, which comprises:

(a) a bendable solid core piece having a control end and a distal end, and having a predeterminded length and a predetermined core diameter;

(b) a tightly held polymeric sleeve, covering said core piece and extending over at least a portion of the distal end of said core piece, said sleeve being formed of a first polymer composition which is a polyacrylonitrile-containing composition; and, (c) a mixture of radio-opaque powder and a second polymer composition contained within said sleeve at said distal end of said core piece forming an area separate from but physically bonded to said sleeve.

16. The guidewire of claim 15 wherein said distal end of said core piece is tapered and said mixture is around said distal end of said core piece.

17. The guidewire of claim 15 wherein said first polymer composition is a polyacrylonitrile-containing copolymer.

18. The guidewire of claim 17 wherein said copolymer is a hydrogel.

19. The guidewire of claim 15 wherein said first polymer composition is a hydrogel.

20. The guidewire of claim 15 wherein said second polymer composition is a polyacrylonitrile-containing composition.

21. The guidewire of claim 15 wherein said second polymer composition is a polyacrylonitrile-containing copolymer.

22. The guidewire of claim 15 wherein said second polymer composition is a hydrogel.

23. The guidewire of claim 15 wherein said first polymer composition and said second polymer composition are both polyacrylonitrile copolymers.

24. The guidewire of claim 23 wherein at least one of said first polymer composition and said second polymer composition are hydrogels.

25. The guidewire of claim 15 wherein said physical bond is a chemical bond between said first polymer composition and said second polymer composition.

26. The guidewire of claim 15 wherein said physical bond is a network polymer interweaving bond.

27. The guidewire of claim 15 wherein said physical bond is a fusion bond.

28. The guidewire of claim 15 wherein said radio-opaque metal powder is selected from one or more non-toxic heavy metals.

29. The guidewire of claim 28 wherein said radio-opaque metal powder is selected from one or more of tungsten, platinum, tantalum and gold.

* * * * *